United States Patent [19]

Rossey et al.

[11] Patent Number: 5,013,835
[45] Date of Patent: May 7, 1991

[54] METHOD OF PREPARING (+)-(2S,3S)-3-HYDROXY-2-(4-METHOXY-PHENYL)2,3-DIHYDRO-5H-1,5-BENZO-THIAZEPINE-4-ONE

[75] Inventors: Guy Rossey, Voisins-Le-Bretonneux; Isaac Chekroun, Epinay; Antonio Ugolini, Le Pecq; Alexander Wick, St. Nom La Breteche; Bernard Gerin, Mantes La Jolie; Andre Bourbon, Mantes La Jolie; Jean-Baptiste Graux, Mantes La Ville, all of France

[73] Assignee: Synthelabo, Paris, France

[21] Appl. No.: 408,042

[22] Filed: Sep. 14, 1989

[51] Int. Cl.$^5$ ............................................. C07D 281/02
[52] U.S. Cl. ...................................................... 540/491
[58] Field of Search ........................................ 540/491

[56] References Cited

U.S. PATENT DOCUMENTS

| | | | |
|---|---|---|---|
| 4,416,816 | 11/1983 | Nagao et al. | 540/491 |
| 4,420,628 | 12/1983 | Inoue et al. | 560/17 |
| 4,438,035 | 3/1984 | Gaino et al. | 540/491 |
| 4,552,695 | 11/1985 | Igarashi et al. | 540/491 |
| 4,885,375 | 5/1989 | Wynberg et al. | 540/491 |

FOREIGN PATENT DOCUMENTS

| | | | |
|---|---|---|---|
| 61-145159 | 12/1986 | Japan | 540/491 |
| 61-145160 | 12/1986 | Japan | 540/491 |
| 61-145174 | 12/1986 | Japan | 540/491 |

OTHER PUBLICATIONS

Hashiyama et al. (1985), J. Chem. Soc. Perkin. Trans., 1: 421–427, Kugita et al. (1970), Chem. Pharm. Bull. 18: 2028–2037.

*Primary Examiner*—Robert T. Bond
*Attorney, Agent, or Firm*—Fleit, Jacobson, Cohn, Price, Holman & Stern

[57] ABSTRACT

2-Aminothiophenol is reacted with (−)-(2R,3S)-2,3-epoxy-3-(4-methoxyphenyl) methylpropionate, and the intermediate (2S,3S)-3-[(2-aminophenyl)thio]-2-hydroxy-3-(4-methoxyphenyl) methylpropionate is then cyclized in the presence of methane sulfonic acid, in the same container and without isolating said intermediate product, using chlorobenzene as a solvent.

2 Claims, No Drawings

METHOD OF PREPARING (+)-(2S,3S)-3-HYDROXY-2-(4-METHOXY-PHENYL)2,3-DIHYDRO-5H-1,5-BENZOTHIAZEPINE-4-ONE

The subject of the present invention is a method for preparing (+)-(2S,3S)-3-hydroxy-2-(4-methoxyphenyl)-2,3-dihydro-5H-1,5-benzothiazepine-4-one.

This optically pure compound is a synthetic intermediary of compounds with therapeutic activities, such as (+)-(2S,3S) -3-acetyloxy-5-(2-dimethylaminoethyl)-2-(4-methoxyphenyl)-2,3-dihydro-5H-1,5-benzothiazepine-4-one.

The reaction diagram of the method is shown on the following page.

The first step comprises reacting 2-aminothiophenol of formula II with (−)-(2R,3S)-2,3-epoxy-3-(4-methoxyphenyl) methylpropionate of formula III. By opening the epoxide cycle, (2S,3S)-3-[(2-aminophenyl)thio]-2-hydroxy-3-(4-methoxyphenyl) methylpropionate of formula IV is obtained.

The second step comprises cyclizing this compound in the presence of acid.

The reaction principles of each of the two steps are well known.

They are found, for example, in Chem. Pharm. Bull., 18, 2028–2037 (1970), where the ester of formula III is used in racemic form. The first step necessitates several hours of heating to 150°-160° C., and after separation and purification of the ester of formula IV, the second step is performed by hydrolyzing this ester and cyclizing the acid obtained in the presence of sulfuric or acetic acid, in xylene in reflux.

U.S. Pat. No. 4,416,819 describes the first method step, where the (racemic) ester of formula III reacts with the aminothiophenol (II) in toluene after six hours of reflux heating.

Japanese Patent Application 145160/1986, which describes the synthesis of the optically pure ester of formula III, likewise describes the reaction of the latter with aminothiophenol of formula II, by heating for 10 hours in reflux in toluene.

Diagram

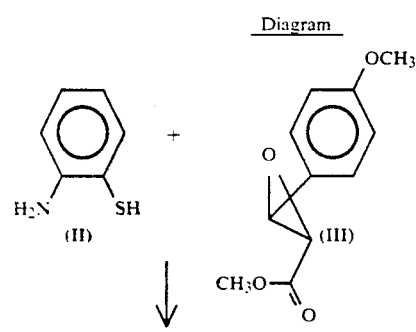

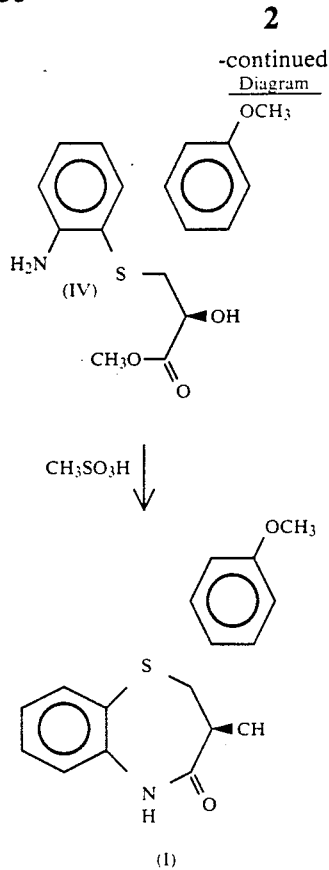

Finally, European Patent Application 0154838 describes among others a method that combines the two steps. The reactions are performed without solvent, requiring 16 hours of heating to 160° C., and furnishing a mixture of optical isomers of the final compound and the intermediate compound.

Thus it is clear that none of the known methods are adapted to an affordable industrial manufacture of the compound of formula I, because of the various disadvantages accompanying them: mediocre yields, elevated temperatures, the necessity of purifying the intermediate and/or final compounds, and long reaction times.

The present invention therefore proposes a method that overcomes the disadvantages of the known art, and affords the following advantages:

the two reaction steps are performed in one and the same reactor, so that evacuating and cleaning it between the two steps is unnecessary, or a second reactor may be used;

the total yield is high compared with the yields of the known methods;

energy consumption is reduced, in particular during the first step;

the reaction times are short; and the final compound is pure.

The physico-chemical conditions of the method according to the invention which make it possible to attain all the advantages listed above are described below.

The starting ester of formula III is used in optically pure form. It is described in Japanese Patent Applications 145159/1986, 145160/1986 and 145174/1986.

The possibility of performing the two steps of the reaction in the same container, without evacuation or intermediate transfer to another vessel, is due to the selection of a unique solvent, which is highly suitable to each of the steps.

Specific solvents for each of the two steps are naturally already known (dichloroethane, toluene, xylene, etc.), but they are different for each step and so do not permit the entire method to take place within the same reactor. The solvent to be used according to the invention is chlorobenzene.

This solvent is not only—and unexpectedly—highly favorable to a good total yield, but furthermore is so efficient that the first method step necessitates heating only for startup, because the exothermic nature of the reaction is sufficient for it to be maintained without adding external energy. This particular feature was entirely unforeseeable, because it had never been found in the use of other solvents.

Additionally, the use of chlorobenzene promotes the threoerythro selectivity of the first step. With other solvents, it is in fact found that a mixture of diastereoisomers of formula IV is obtained.

Another particular feature of the invention is due to the catalyst used in the second method step. While it is known that cyclization takes place better in an acid medium (sulfuric or acetic), the catalyst to be used according to the invention is methane sulfonic acid. This acid, which makes it possible to obtain an excellent yield, is simple to add to the reaction medium as soon as the first step is completed.

The example that follows provides a detailed illustration of one way of performing the method according to the invention.

EXAMPLE

In an enameled 25-liter reactor, purged with nitrogen, 3 kg of (−)-(2R, 3S)-2,3-epoxy-3-(4-methoxyphenyl) methylpropionate and 10 l of chlorobenzene are introduced, and the mixture is heated to 100° C. Heating is stopped, and in the space of 30 minutes, so as not to allow the temperature to exceed 120° C. a solution of 1900 g of 2-aminothiophenol in 1.5 l of chlorobenzene is introduced, and then 3.5 l of chlorobenzene is also added to rinse the inlet funnel and the tubing.

The temperature is kept at approximately 115° C. for a further 30 minutes, and then 37.5 ml of methane sulfonic is added, and the mixture is heated in reflux for 8 hours, eliminating a mixture of methanol and chlorobenzene by distillation, in order not to allow the temperature to drop below 132° C. (the boiling point of chlorobenzene).

The heating is stopped; the mixture is allowed to return to 20° C.; it is chilled to 5° C. for one hour; and the crystals formed are filtered by rinsing them with chlorobenzene, and they are dried in a vacuum at 100° C.

The result obtained is 3463 g of pure (+)-(2S,3S) -3-hydroxy-2-(4-methoxyphenyl)-2,3-dihydro-5H-1,5-benzothiazepine-4-one.

Melting point: 200.3–201.8° C. $[\alpha]_D^{30} = +114°$ (c=0.1; DMF).

We claim:

1. A method of preparing (+)-(2S,3S) -3-hydroxy-2-(4-methoxyphenyl)-2,3-dihydro-5H-1,5-benzothiazepine-4-one, comprising:
    (a) reacting 2-aminothiophenol with (−) -(2R,3S)-2,3-epoxy-3-(4-methoxyphenyl)methylpropionate to yield the intermediate (2S, 3S)-3-[2-aminophenyl)thiol -2-hydroxy-3-(4-methoxyphenyl)methylpropionate; and then, without isolating said intermediate,
    (b) cyclizing said intermediate in the presence of acid, wherein said reacting and cyclizing steps are performed in the presence of chlorobenzene, whereby step (b) is performed without isolation of said intermediate.

2. The method of claim 1, wherein said acid is methane sulfonic acid.

* * * * *

UNITED STATES PATENT AND TRADEMARK OFFICE
CERTIFICATE OF CORRECTION

PATENT NO.   : 5,013,835
DATED        : May 7, 1991
INVENTOR(S)  : Guy ROSSEY et al

It is certified that error appears in the above-identified patent and that said Letters Patent is hereby corrected as shown below:

[30]         Foreign Application Priority Data

Jan. 11, 1989  [FR]  France ............... 89 00246

UNITED STATES PATENT AND TRADEMARK OFFICE
CERTIFICATE OF CORRECTION

PATENT NO. : 5,013,835

DATED : May 7, 1991

INVENTOR(S) : Guy ROSSEY et al

It is certified that error appears in the above-identified patent and that said Letters Patent is hereby corrected as shown below:

Column 1, lines 60-65 (formula III):

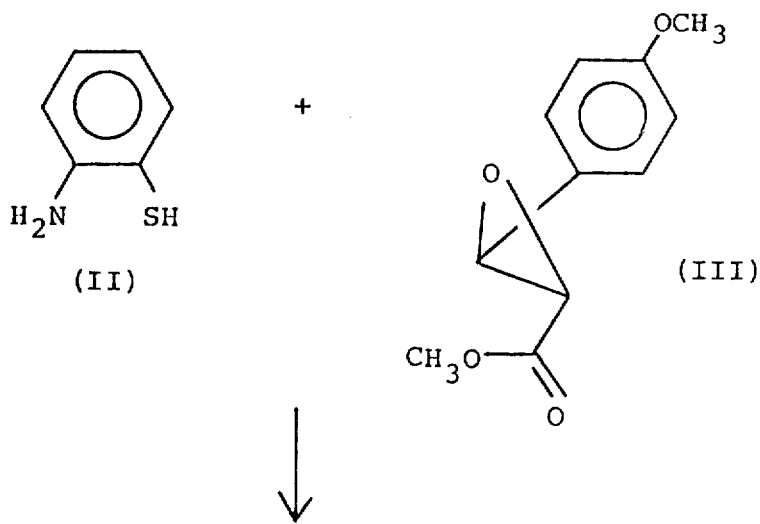

UNITED STATES PATENT AND TRADEMARK OFFICE
CERTIFICATE OF CORRECTION

PATENT NO. : 5,013,835

DATED : May 7, 1991

INVENTOR(S) : Guy ROSSEY et al

It is certified that error appears in the above-identified patent and that said Letters Patent is hereby corrected as shown below:

Column 2, lines 5-30 (formulas IV and I):

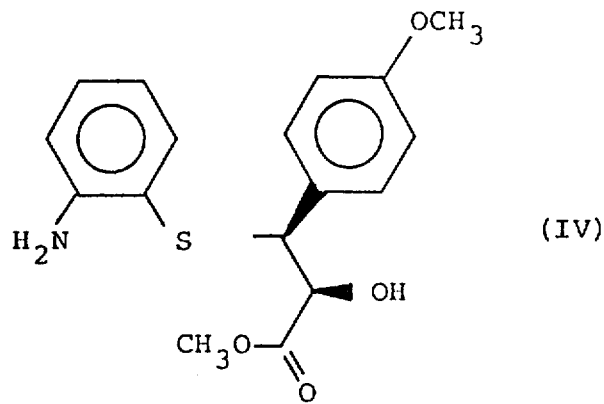

(IV)

$CH_3SO_3H$ ↓

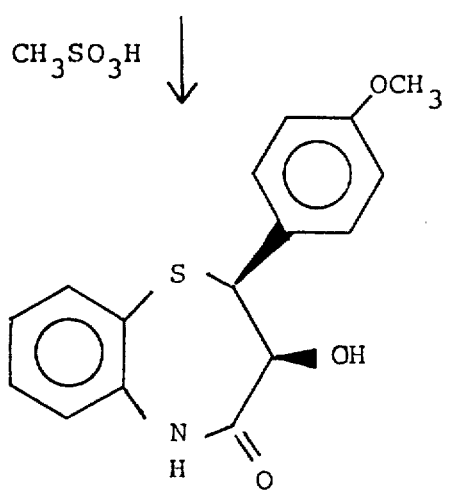

(I)

UNITED STATES PATENT AND TRADEMARK OFFICE
CERTIFICATE OF CORRECTION

PATENT NO. : 5,013,835
DATED : May 7, 1991
INVENTOR(S) : Guy ROSSEY et al

It is certified that error appears in the above-identified patent and that said Letters Patent is hereby corrected as shown below:

Column 3, line 18, "threoerythro" should read:

--threo-erythro--.

Column 4, line 19, "$[\alpha]_D^{30}$" should read:

--$[\alpha]_D^{20}$--.

Column 4, line 30, "phenyl)thiol" should read:

--phenyl)thio]--.

Signed and Sealed this

Sixteenth Day of March, 1993

Attest:

STEPHEN G. KUNIN

Attesting Officer

Acting Commissioner of Patents and Trademarks